United States Patent
Salisbury et al.

(10) Patent No.: US 6,433,344 B1
(45) Date of Patent: *Aug. 13, 2002

(54) PULSED LIGHT STERILIZATION OF DRINKING WATER AND DRINKING WATER CONTAINERS

(75) Inventors: Kenton J. Salisbury, San Diego; Ted H. Toch, Coto de Caza, both of CA (US)

(73) Assignee: Purepulse Technologies, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/545,935

(22) Filed: Apr. 10, 2000

Related U.S. Application Data

(63) Continuation-in-part of application No. 09/326,168, filed on Jun. 4, 1999, which is a continuation-in-part of application No. 08/846,102, filed on May 1, 1997, now Pat. No. 5,925,885, which is a continuation-in-part of application No. 08/651,275, filed on May 22, 1996, now Pat. No. 5,786,598.

(51) Int. Cl.$^7$ .............................. B65B 55/08; A61L 2/10
(52) U.S. Cl. ............................. 250/455.11; 250/492.1; 422/24
(58) Field of Search ..................... 250/455.11, 492.1; 422/24

(56) References Cited

U.S. PATENT DOCUMENTS

| | | |
|---|---|---|
| 3,817,703 A | 6/1974 | Atwood |
| 4,063,890 A | 12/1977 | Baron ........................... 21/54 |
| 4,282,863 A | 8/1981 | Beigler et al. ............... 128/1 R |
| 4,304,996 A | 12/1981 | Blades ........................ 250/373 |
| 4,327,276 A | 4/1982 | Injushin et al. ............. 219/121 |
| 4,464,336 A | 8/1984 | Hiramoto ..................... 422/24 |
| 4,469,835 A | 9/1984 | Laurin ......................... 524/349 |

(List continued on next page.)

FOREIGN PATENT DOCUMENTS

| | | |
|---|---|---|
| GB | 2141723 | 1/1985 |
| GB | 2117733 | 10/1993 |
| WO | 8201703 | 5/1982 |
| WO | 8803369 | 5/1988 |
| WO | 9516565 | 6/1995 |

OTHER PUBLICATIONS

Dunn et al., "Pulsed Light Treatment of Food and Packaging", *Food Technology*, vol. 49:9, pp. 95–98 (Sep. 1995).

*Primary Examiner*—Jack Berman
(74) *Attorney, Agent, or Firm*—Fitch, Even, Tabin & Flannery

(57) ABSTRACT

An approach for sterilizing microorganisms at a drinking water container employs a flashlamp system including means for generating pulses of light, and for deactivating microorganisms within the drinking water container by illuminating the drinking water container with the pulses of light having been generated; a photo-sensitive detector positioned so as to receive a portion of each of the pulses of light as a measure of an amount of light illuminating the drinking water container, for generating an output signal in response thereto; and a control system, coupled to the flashlamp system and the photo-sensitive detector, for determining, in response to the output signal, whether the pulses of light are sufficient to effect a prescribed level of deactivation of microorganisms in the drinking water container. In accordance with this approach sterilizing microorganisms involves steps of generating a pulse of light; deactivating microorganisms at the drinking water container by directing the pulse of light having been generated at the drinking water container; receiving a portion of the pulse of light as a measure of an amount of the pulse of light illuminating the drinking water container; generating an output signal in response to the receiving of the portion of the pulse of light; and determining, in response to the generating of the output signal, whether the pulse of light is sufficient to effect a prescribed level of deactivation of microorganisms in the drinking water container.

46 Claims, 6 Drawing Sheets

U.S. PATENT DOCUMENTS

| | | | |
|---|---|---|---|
| 4,540,416 A | 9/1985 | Hattori et al. | 604/410 |
| 4,629,658 A | 12/1986 | Lucas | 428/520 |
| 4,657,540 A | 4/1987 | Iwamoto | 604/408 |
| 4,866,282 A | 9/1989 | Miripol et al. | 250/455 |
| 4,871,559 A | 10/1989 | Dunn et al. | 426/248 |
| 4,910,942 A | 3/1990 | Dunn et al. | 53/425 |
| 5,034,235 A | 7/1991 | Dunn et al. | 426/238 |
| 5,122,126 A | 6/1992 | Sakakiyama | 604/415 |
| 5,129,894 A | 7/1992 | Sommermeyer et al. | 604/408 |
| 5,324,233 A | 6/1994 | Owensby et al. | 493/190 |
| 5,364,645 A | 11/1994 | Lagunas-Solar et al. | 426/248 |
| 5,441,179 A | 8/1995 | Marsh | 222/190 |
| 5,494,155 A | 2/1996 | Evans et al. | 206/204 |
| 5,607,593 A * | 3/1997 | Cote et al. | 210/636 |
| 5,658,530 A | 8/1997 | Dunn | 422/24 |
| 5,730,934 A | 3/1998 | Holbert | 422/24 |
| 5,744,094 A | 4/1998 | Castberg et al. | 422/24 |
| 5,768,853 A | 6/1998 | Bushnell et al. | 53/167 |
| 5,786,598 A | 7/1998 | Clark et al. | 250/455.11 |
| 5,900,211 A | 5/1999 | Dunn et al. | 422/24 |
| 5,916,439 A | 6/1999 | Oleskow | 210/198.1 |
| 5,925,885 A | 7/1999 | Clark et al. | 250/492.1 |
| 6,013,918 A | 1/2000 | Bushnell et al. | 250/454.11 |

* cited by examiner

PULSED LIGHT STERILIZATION OF DRINKING WATER AND DRINKING WATER CONTAINERS

RELATED APPLICATIONS

This application is a continuation-in-part (CIP) of U.S. Ser. No. 09/326,168, filed Jun. 4, 1999, for PARAMETRIC CONTROL IN PULSED LIGHT STERILIZATION which is a continuation-in-part (CIP) of U.S. Ser. No. 08/846,102, filed May 1, 1997, now U.S. Pat. No. 5,925,885 for PARAMETRIC CONTROL IN PULSED LIGHT STERILIZATION OF PACKAGES AND THEIR CONTENTS, issued Jul. 22, 1999 which is a continuation-in-part (CIP) of U.S. Ser. No. 08/651,275, filed May 5, 1996, for STERILIZATION OF PACKAGES AND THEIR CONTENTS USING HIGH-INTENSITY, SHORT-DURATION PULSES OF INCOHERENT, POLYCHROMATIC LIGHT IN A BROAD SPECTRUM, now U.S. Pat. No. 5,786,598, issued Jul. 5, 1998, all three of which are incorporated herein by reference.

BACKGROUND OF THE INVENTION

The present invention relates to sterilization of drinking water and drinking water containers by inactivation of microorganisms located therein and/or thereon. More particularly, the present invention relates to sterilization of drinking water and drinking water bottles using pulsed light sterilization of sealed drinking water bottles. Also described herein, are methods and apparatus for the sterilization of drinking water and drinking water containers by deactivation of microorganisms in drinking water or on said drinking water containers including sterilization of drinking water after being sealed within a drinking water container, using high-intensity, short-duration pulses of incoherent, polychromatic light in a broad spectrum. Finally, the present invention relates to monitoring and controlling key pulsed light parameters to verify sterilization has been achieved.

Various methods of sterilization are known to those of skill in the art, including for example, heat sterilization, e.g., autoclaving, irradiation sterilization, e.g., using gamma radiation, and chemical sterilization. These conventional methods are unsuited to the sterilization of drinking water for a variety of reasons.

A typical drinking water purification process as currently practiced in the art treats water with a series of filters and perhaps other water treatment devices. After filtration and treatment the drinking water is containerized. For example, a water source is provided which introduces drinking water into a multimedia filter which the directs the filtered water into, for example, an activated carbon filter which directs the twice filtered water into a cartridge filter, for example, a 1 $\mu$m filter. This thrice filtered drinking water can then be treated with UV radiation or ozone treated before being introduce to a drinking water container which is filled and capped. This allows ample opportunity for post filtration/treatment contamination of the drinking water. Numerous other water treatment schemes have been tried but none have the advantage of being able to treat drinking water after it has been sealed within its container.

A more recently developed, and hence less well known, method of deactivating microorganisms on and/or within target objects uses high-intensity, short-duration pulses of incoherent, polychromatic light in a broad spectrum to sterilize target objects.

The polychromatic light sterilization techniques and apparatus embodied in the present invention has several significant advantages over conventional sterilization techniques. The first being that the present invention accomplishes sterilization far more quickly than conventional methods. The embodiments of the present invention can sterilize most drinking water and most sizes of drinking water containers in less than a few minutes, as only a few flashes, having durations of a few seconds to less than a minute, are required to achieve sterilization. Second, high-intensity, short-duration pulses of incoherent, polychromatic light can achieve a degree of sterility not possible with current drinking water purification techniques. Also, the embodiments of the present invention accomplish this goal with a higher degree of reliability than purification techniques commonly used to purify drinking water. Third, the present embodiments accomplish these goals using less floor space and at less cost.

An example of these advantages is demonstrated by comparison with the current best method of sterilization, autoclaving. Autoclaving requires, a great deal of time to complete (2–3 hours) and has a high energy cost associated with water heating. Moreover, to autoclave the large amounts of water needed in commercial drinking water applications requires huge amounts of floor space to house the autoclaving machines. These cost and space constraints are so prohibitive that autoclaving is not used to purify drinking water. The methods and embodiments of the present invention allow high volume sterilization of drinking water and drinking water containers in a much smaller space than autoclaving while taking far less time.

A further limitation of conventional methods of terminal sterilization, such as autoclaving, is that they are unsuitable for use with polyethylene containers or thin polypropylene containers, because such containers are unable to withstand the temperatures (e.g., between 100 and 200° C.) or pressures of autoclaving (polypropylene containers are able to withstand some amount of commercially useful autoclaving, however, they are required to be thicker and more expensive to withstand autoclaving than would need be in the absence of this high heat and pressure treatment). Thus, there exists a need for an approach to deactivating microorganisms in drinking water through a container that does not require the use of heat that may damage the container or its contents.

The embodiments of the present invention can sterilize drinking water contained in many different types of packaging materials, such as olefins (e.g., polyethylene or polypropylene); nylon, or a composite material, either laminated or co-extruded structure (including both monolayer and multilayer structures), and the like. The term container as used herein is intended to be interpreted broadly, including but not limited to, bags, bottles, hoses, tubes, water feed lines, or other means of containing drinking water.

Other sterilization processes, e.g., using gamma radiation to achieve terminal sterilization can damage the polymeric structure of olefin containers (i.e., gamma radiation degrades container integrity), which can result in weakened container integrity, leakage, increased gas permeability and other such problems. Gamma radiation can also attack the container and/or its contents to produce other adverse changes, such as darkening, off-colors or color changes, etc. in the container or its contents. Furthermore, gamma radiation inherently causes the generation of highly reactive species, such as hydroxyl radicals, during the gamma irradiation of water, that may detrimentally alter the chemical structure of the product being treated. Thus, there exists a need for an improved sterilization process usable with polyolefins and the like that does not employ gamma radiation, or other such reactive processes, to achieve sterilization.

Other problems with heat treatment, i.e., autoclaving, and conventional gamma radiation treatment techniques include the "batch" nature of such processes. Specifically, with heat or gamma radiation treatment, product containers are treated in groups or batches, which problematically requires additional handling of the product not required if an on-line continuous process is used. In addition, careful inventorying and product handling are required in order to assure that each batch is segregated, and separately treated and tested.

Using conventional terminal sterilization techniques it is nearly impossible to monitor all of the parameters necessary to assure adequate deactivation of microorganisms in all of the product containers in a given batch (i.e., parametric control is nearly impossible). (For example, it is difficult to monitor the temperature within the autoclave at enough points so than one can assure that every part of every container in the batch received enough heat and saturated steam pressure to achieve adequate deactivation of microorganisms.) Because such parametric control is not generally possible with heretofore employed terminal sterilization techniques, such containers must be observed after treatment, e.g., a fourteen day period following terminal sterilization to determine whether any contaminants are present in selected (or all) containers from each batch. This unfortunately further complicates product and product container treatment and delays usage of the containers and products having been treated. An approach that can be performed in a continuous manner, e.g., as a part of a packaging process, thus eliminating the need for "batch" handling and "batch" testing; and an approach that allows adequate parametric control over processing parameters needed to assure adequate sterility levels, thus eliminating the need for an observation period following treatment, would be highly advantageous.

A generally accepted standard for sterility is, for example, less than one in a million ($10^{-6}$) survivor probability among microbial contaminants. In other words, there must be less than once chance in a million that viable microorganisms are present in a sterilized article. This level of sterilization is referred to as a sterility assurance level of $10^{-6}$. Until now, this level of sterility has not be achievable in a practical sense in drinking water.

In addition to the difficulties inherent in achieving the requisite sterility in drinking water by conventional methods, is the ability to verify that such sterility levels have been attained. Ordinarily, "sterilized" containers must be observed for a period of time, e.g., for fourteen days, following terminal sterilization to determine whether any contaminants are present. This, unfortunately, further complicates drinking water treatment processing and further increases the processing time. An approach that can be performed in a continuous manner, e.g., as a part of a packaging process, can eliminate the need for batch handling and batch testing. Moreover, a sterilization approach that allows adequate parametric control over processing parameters to assure adequate sterility levels can eliminate the need for an observation period following treatment.

Therefore, what is needed is an approach to rapidly deactivating microorganisms inside a sealed drinking water container which achieves an easily verifiable sterility assurance level of at least, for example, $10^{-6}$, but which approach also reduces damage to the drinking water container.

The present invention advantageously addresses the above and other needs.

SUMMARY OF THE INVENTION

The present invention advantageously addresses the needs above as well as other needs by providing an approach for deactivating microorganisms, and more particularly for the deactivating of microorganisms within drinking water containers, and within the drinking water contents of such containers, using high-intensity, short-duration pulses of incoherent, polychromatic light in a broad spectrum directed at the containers, filled and/or empty, so as to penetrate the containers and deactivate microorganisms inside said container, particularly on interior container surfaces and/or suspended in the volume of drinking water contained within the containers.

In one embodiment, the invention can be characterized as an apparatus for sterilizing microorganisms in a container. Such apparatus employs the container, which includes a polyolefin, and which transmits light in a spectrum containing wavelengths selected from between 120 nm and 2600 nm, e.g., wavelengths between 180 nm and 1500 nm or, e.g., between 180 nm and 380 nm. The container may include an input port through which drinking water may be introduced into the container. The port may include threads onto which a threaded cap may be screwed and secured. Typically, the cap is unscrewed or otherwise removed before introduction of drinking water. Such input ports are well known in the art. A flashlamp system generates high-intensity, short-duration pulses of polychromatic light in a broad spectrum, and the pulses of light generated by the flashlamp illuminate the container and deactivate microorganisms within the container.

In a variation of this embodiment, the input port is specifically illuminated and microorganisms within the port are deactivated by the high-intensity, short-duration pulses of incoherent, polychromatic light in a broad spectrum.

In a still further embodiment, the invention can be characterized as an apparatus for sterilizing microorganisms in a drinking water container, wherein said container may include, for example, a polyolefin, such as polyethylene, and which transmits light in a spectrum containing wavelengths selected from between about 120 nm and about 2600 nm, e.g., wavelengths between 180 nm and 1500 nm or, e.g., between 180 nm and 300 nm. A flashlamp system generates high-intensity, short-duration pulses of polychromatic light in a broad spectrum, and the pulses of light generated by the flashlamp illuminate the drinking water container and deactivate microorganisms within the drinking water container.

In another embodiment, the invention may be characterized as an apparatus for deactivating microorganisms in a container which contains transmissive drinking water that transmits more than about one percent of light at a wavelength of 260 nm, and which container transmits light in a spectrum having wavelengths selected from between 120 nm and 2600 nm (see examples above). The embodiment also employs an input port coupled to the container through which the drinking water can be introduced into the container, and a flashlamp system that generates high-intensity, short-duration pulses of polychromatic light in a broad spectrum, and deactivates microorganisms within the container by illuminating the container with such pulses of light.

In an additional embodiment, the invention can be characterized as an apparatus for deactivating microorganisms in a container which includes a container having at least one input port through which the drinking water can be introduced into the container, and transmits light in a spectrum having wavelengths selected from between 120 nm and 2600 nm (see examples above); a flashlamp system that generates high-intensity, short-duration pulses of polychromatic light in a broad spectrum, and deactivates microorganisms within the container by illuminating the container with the pulses of light having been generated. The flashlamp of this embodiment advantageously deactivates sufficient microorganisms to achieve a sterility assurance level of at least $10^{-6}$.

In an even further embodiment, the present invention can be characterized as an apparatus for sterilizing microorganisms at in a drinking water container. Such apparatus employs a flashlamp system including means for generating high-intensity, short-duration pulses of polychromatic light in a broad spectrum, and for deactivating microorganisms within the drinking water container by illuminating the drinking water container with the pulses of light having been generated; a photo-sensitive detector positioned so as to receive a portion of each of the pulses of light as a measure of an amount of light illuminating the drinking water container, for generating an output signal in response thereto; and a control system, coupled to the flashlamp system and the photo-sensitive detector, for determining, in response to the output signal, whether the pulses of light are sufficient to effect a prescribed level of deactivation of microorganisms in the drinking water container.

In still a further embodiment, the present invention can be characterized as a method for sterilizing microorganisms in a drinking water container, having steps of generating a high-intensity, short-duration pulse of polychromatic light in a broad spectrum; deactivating microorganisms at the drinking water container by directing the pulse of light having been generated at the drinking water container; receiving a portion of the pulse of light as a measure of an amount of the pulse of light illuminating the drinking water container; generating an output signal in response to the receiving of the portion of the pulse of light; and determining, in response to the generating of the output signal, whether the pulse of light is sufficient to effect a prescribed level of deactivation of microorganisms in the drinking water container. This embodiment includes a further embodiment wherein said output signal used to determine whether a prescribed level of deactivation of microorganisms in the drinking water container has been achieved, validates the sterilization process such that a sterility assurance level of at least about $10^{-6}$ is achieved.

Further provided herein is a method of optimizing deactivation of microorganisms on and/or within a drinking water container, using high-intensity, short-duration pulses of polychromatic light in a broad spectrum, by automatically adjusting the intensity and/or duration of light exposure based upon parametric detection of the light. In particular, a photo-sensitive detector is employed to receive a portion of each pulse of light as a measure of the amount of light illuminating the drinking water container and that measurement is used to calculate the degree of deactivation of microorganisms occurring at the surface and/or within the drinking water container. In response to the measurements taken and calculations made, the intensity and/or duration of the pulsed light is adjusted to provide optimized deactivation. Further, these measurements can be, quite advantageously, used to validate sterilization of the drinking water container.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE PREFERRED EMBODIMENTS

The following description of the presently contemplated best mode of practicing the invention is not to be taken in a limiting sense, but is made merely for the purpose of describing the general principles of the invention. The scope of the invention should be determined with reference to the claims.

Figure 1:
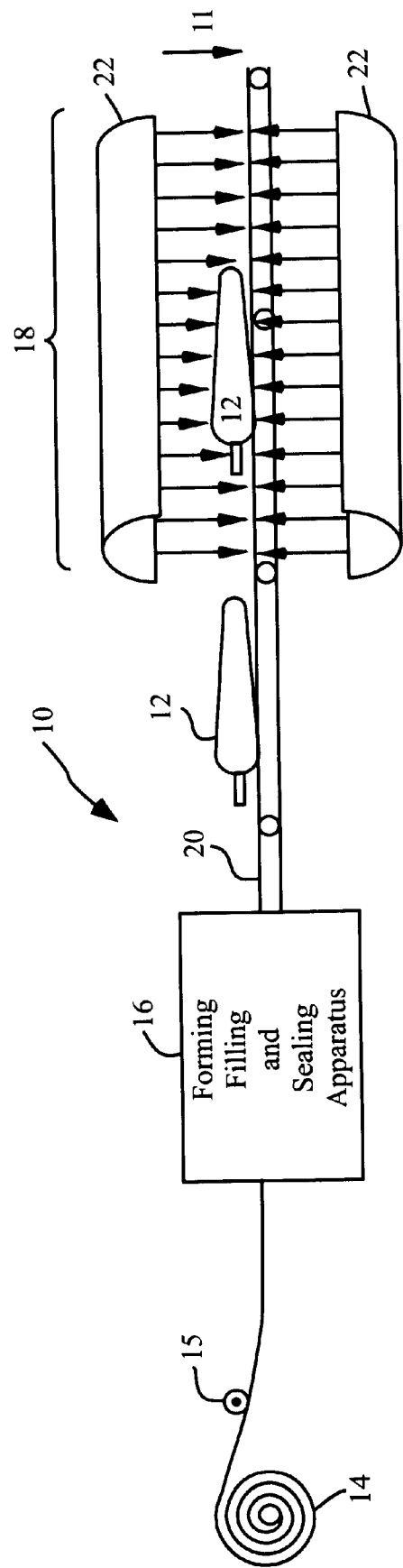
FIG. 1 is a schematic diagram of an apparatus for fabricating, filling, sealing and sterilizing a drinking water container.

Referring first to FIG. 1, the diagram of an apparatus 10 for fabricating, filling, sealing, and sterilizing a drinking water container 12 is shown. A roll 14 (or other supply) of packing material is fed by, for example, rollers 15, into a fabricating, filling and sealing apparatus 16, such as are known in the art. Alternatively, the packaging material may assume a form of resin beads, as would be the case typically in a blow/fill/seal apparatus. The fabricating, filling and sealing apparatus 16 may be a form/fill/seal apparatus; a blow/fill/seal apparatus; an injection blow molding apparatus; an extrusion and coextrusion blow molding apparatus; a film/sheet extrusion and coextrusion apparatus; a thermoforming apparatus; or an injection molding apparatus, such as are known in the art. Various sealing equipment and techniques may be employed including heat sealing, radio frequency (RF) fabrication, hot plate welding, induction welding, and/or spin welding, all of which are well known in the art.

Also shown, is a treatment zone, or sterilization tunnel, 18 (sterilizing chamber 18) through which fabricated, filled and sealed drinking water containers are passed, by, for example, a conveyer belt 20 or other appropriately transmissive conveyance component, in order to sterilize such containers. The conveyer belt 20 may employ one or more quartz shelves on which the drinking water containers rest while they are conveyed, or one or more hooks from which the drinking water containers hang while they are conveyed. In this way, the drinking water containers are not shielded from light as they pass through the sterilizing chamber 18.

The forming, filling and sealing apparatus 16 may, as mentioned above, be of a type well-known in the art, and preferably is capable of manufacturing containers (or containers) at high speeds, and with from one to multiple cavitations.

One example of a suitable blow/fill/seal apparatus adaptable for use with the present embodiment is marketed under Model No. 603 by Automatic Liquid Packaging, Inc. of Illinois. Another such apparatus is marketed under Model No. 624 by Automatic Liquid Packaging of Illinois. Also, a suitable form/fill/seal apparatus utilizes an extruded film to form a container. One example of such a form/fill/seal apparatus adaptable for use with the present embodiment is marketed as System Model Mark III by Inpaco of Pennsylvania.

The sterilizing chamber 18, as shown, may consist of one or more reflectors 22, and one or more flashlamps (not shown), such as are available as Part No. 2655-501 from PurePulse Technologies, Inc. of San Diego, Calif. Such flashlamps and attendant pulse-generating hardware (not shown) are capable of generating high-intensity, short-duration pulses of incoherent polychromatic light in broad spectrum. Suitable flashlamps and attendant pulse generating hardware are described in U.S. Pat. No. 4,871,559 (METHODS FOR PRESERVATION OF FOODSTUFFS); U.S. Pat. No. 4,910,942 (METHODS FOR ASEPTIC PACKAGING OF MEDICAL DEVICES); and U.S. Pat. No. 5,034,235 (METHODS FOR PRESERVATION OF FOODSTUFFS), issued to Dunn, et al. (the '559, '942 and '235 patents, respectively), incorporated herein by reference as if set forth in their entirety. As will be appreciated by the skilled artisan, numerous known and yet-to-be-developed variations of the flashlamps and pulse generating hardware are suitable for use in the embodiments disclosed herein.

The one or more reflectors 22 direct light from the flashlamps toward completed drinking water containers 12. Preferably, the reflectors 22 are made from, for example, aluminum, and optimally reflect light across the entire spectrum of light generated by the flashlamps. Advantageously, the reflectors may be designed, using commonly known design techniques, to create a uniform or non-uniform energy distribution of light across the drinking water container being illuminated. In this way, for example, greater amounts (i.e., concentrations) of light energy can be directed, for example, at thicker portions of the drinking water container, such as around an input port of the drinking water container; and/or at drinking water contained therein, such as near the middle of the drinking water container where a greater volume of water needing treatment is present.

In accordance with the present embodiment, the pulses of light pass through the drinking water containers 12, reaching the drinking water within the containers, and effecting sterilization or deactivation of microorganisms in the interior of the containers 12 and suspended in the drinking water contained in the containers 12.

In this way, an effective method is provided for sterilizing, not only drinking water containers, but the drinking water contained therein, without requiring the high temperature processes involved in autoclaving. As a result, materials such as olefins, nylon, and composite materials may advantageously be employed in drinking water containers, instead of more conventional materials, such as polyvinyl chloride (PVC) or polyethylterephthalate (PET). Because olefins, nylon, and composite materials have superior moisture vapor barrier characteristics to those of PVC, and do not readily leach contaminants into drinking water, the above apparatus and attendant methods, provide a vastly superior forming, filling, sealing and sterilizing approach than has heretofore been available. Furthermore, the present embodiment can achieve a sterility assurance level of at least $10^{-6}$, and does not require the use of gamma radiation or other highly degradative processes.

Figure 2:
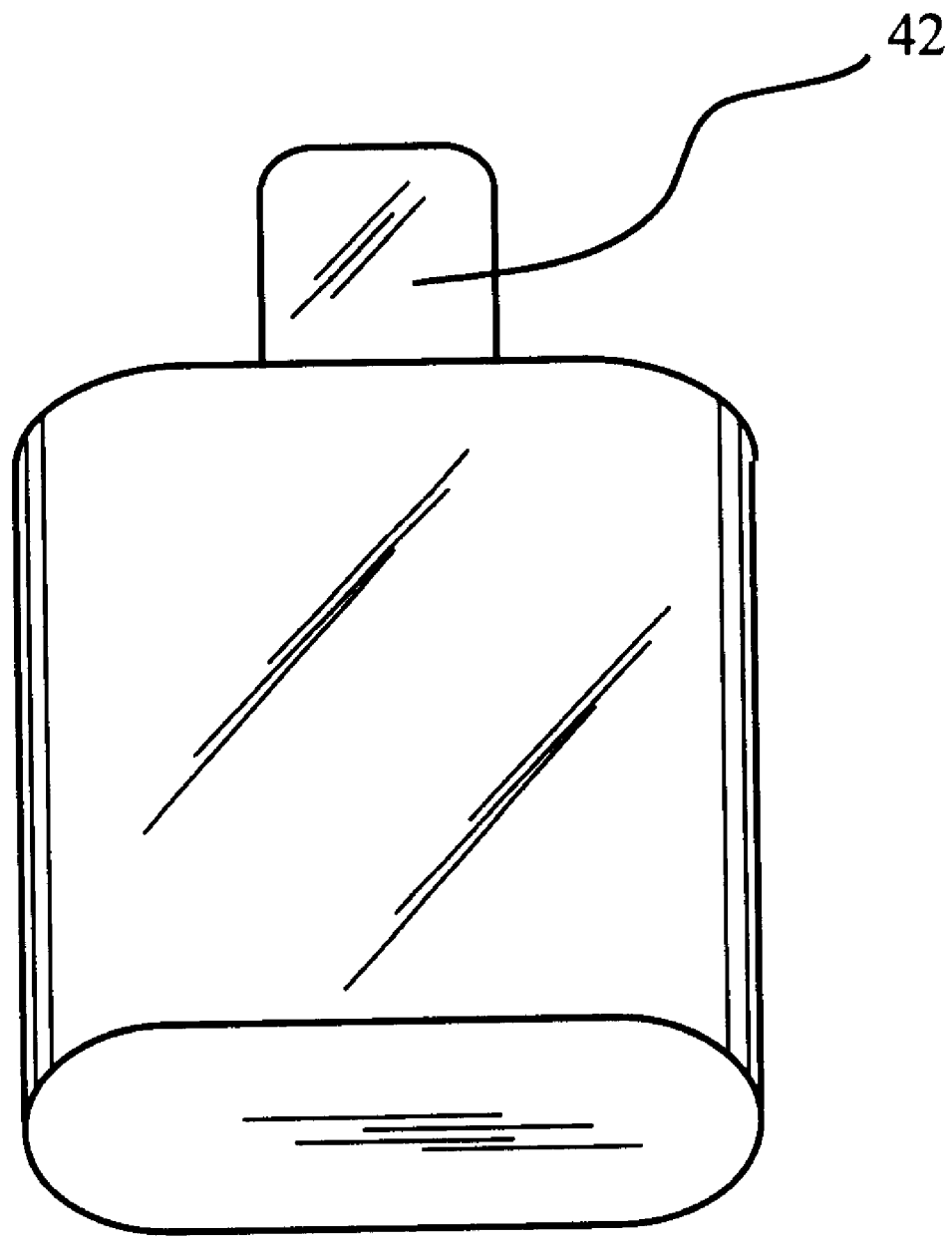
FIG. 2 is a side view diagram of an exemplary drinking water container suitable for use in a sterilizing chamber (or tunnel) of the apparatus of FIG. 1.

Referring to FIG. 2, a typical drinking water container 12 configuration is shown (generically referred to herein as a bottle or container 12). The bottle 12 is typically constructed from polyolefin materials, such as polyethylene. The bottle 12 generally includes an input port 42, through which drinking water can be introduced into the bottle 12, also the input port 42 can be threaded for the attachment of a cap.

The bottle 12 is preferably constructed of materials that transmit light in a spectrum of from, for example, between 180 nm and 1500 nm. Many materials, such as polyethylene, polypropylene, EVOH, nylon and a number of other plastic materials, either monolayer or multilayer, readily transmit this spectrum and can be used, in accordance with variations of the present embodiment.

Figure 3:
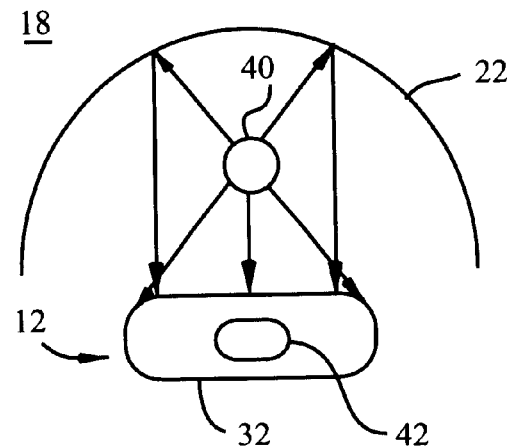
FIG. 3 is an end view of an embodiment of a single reflector sterilizing chamber of the of the present invention having a drinking water container positioned therein.

Referring next to FIG. 3, which depicts an end view of a single reflector sterilizing chamber 18 as can be used with the apparatus of FIG. 1. In the variation shown, a single reflector 22 is positioned around a flashlamp 40 and above a drinking water bottle 12 as it is passed through the sterilizing chamber using, for example, a conveyor belt (not shown).

With continued reference to FIG. 3, in accordance with the present embodiment, high-intensity, short-duration pulses of polychromatic light in a broad spectrum are directed at the drinking water bottle 12 and its attendant input port 42 as they pass through the sterilizing chamber 18. The high-intensity, short-duration pulses of incoherent polychromatic light have an intensity, duration, and wavelength or wavelengths as follows: intensity of from 0.01 J/cm$^2$ to 50 J/cm$^2$, e.g., 0.05 J/cm$^2$ to 5 J/cm$^2$, e.g., 2 J/cm$^2$; duration of from 0.001 ms to 100 ms, e.g., 0.3 ms; and wavelengths selected from between 120 nm and 2600 nm, e.g., wavelengths between 180 nm and 1500 nm or, e.g., between 180 nm and 300 nm. The high-intensity, short-duration pulses of incoherent polychromatic light penetrate the bottle 12, which is substantially transparent to light having wavelengths in the range selected, and impinge upon the drinking water contained therein. As a result, microorganisms at the interior of the bottle 12 and suspended in the drinking water are deactivated.

In some cases, the input port 42 may not be sufficiently transmissive to permit complete sterilization of the input port 42 with the high-intensity, short-duration pulses of polychromatic light in a broad spectrum. However, if a sufficiently transmissive material is selected for the input port 42, and if an appropriate shape and thickness for the input port 42 is selected, such input port 42 can be sufficiently sterilized with high-intensity, short-duration pulses of polychromatic light in a broad spectrum. Selection of a input port design suitable for sterilization using high-intensity, short-duration pulses of polychromatic light in a broad spectrum is well within the abilities of the skilled artisan.

The above-described pulsed light process uses high-intensity, short-duration pulses of polychromatic light in a broad spectrum, i.e., "white" light, to kill a wide range of microorganisms, including microbial and fungal spores. During each flash, the intensity of the light is about 20,000 times the intensity of sunlight at the earth's surface, i.e., the "high-intensity" of the light is from between 0.01 J/cm$^2$ to 50 J/cm$^2$, e.g., 0.05 J/cm$^2$ to 5 J/cm$^2$ or 2 J/cm$^2$, measured at the microorganisms to be deactivated. Each pulse, or flash, of light has a duration of only a fraction of a second (e.g., a "short duration" of from between 0.001 ms to 100 ms, e.g., 0.3 ms).

The flashes are typically applied at a rate of about 1–20 flashes per second and, for most applications, a few, i.e., 1–3, flashes applied in a fraction of a second provide a very high level of microorganism deactivation, or kill. The duration of the light pulses is typically from between 200 and 300 μs.

The process of the present embodiment uses a technique referred to herein as pulsed energy processing. By storing electrical energy in a high energy density electrical storage capacitor, and releasing it in high-energy, short-duration pulses, high peak power levels are achieved. Such high-peak, power levels of electrical energy can be used to create the high-intensity, short-duration pulses of polychromatic light in a broad spectrum. (Pulsed energy processing is described in the '559, '942 and '235 patents, previously incorporated herein by reference.) The high intensity and broad spectrum of these pulses of light results in a unique bactericidal effect not observed when the same energy is provided at low intensity in sustained or continuous applications. Although the peak power of each pulse is preferably very high, because of its short duration, the total energy in each pulse is relatively low, and the average power requirement ("wall plug power") is modest. Thus, the process is not only effective, but is economical with respect to energy consumption.

The pulses of light are generated by electrically ionizing a xenon gas lamp, causing it to emit broad band "white" light. A suitable flashlamp system for use with the present embodiment is readily available as Model No. PBS-1 or PBS-2 from Pure Pulse Technologies of San Diego, Calif., which model utilizes flashlamps, such as are, for example, available as Part No. 2655-501 from PurePulse Technologies, Inc. of San Diego, Calif. The emitted light pulses have wavelengths of from the far ultraviolet (200–300 nm), through the near ultraviolet (300–380 nm), and visible (380–780 nm), to the infrared (780–1100 nm). Approximately 25% of the energy distribution is ultraviolet, 45% of the energy distribution is visible, and 30% of the energy distribution of the light is infrared. Because only one to a few, i.e., 1–3, flashes of light are required to achieve microbial kill, and can be delivered in a very short period of time, this process can be administered very rapidly, and is usable in high throughput applications such as high volume drinking water sterilization.

The light is non-ionizing, and does not penetrate opaque materials, but is transmitted through many packaging materials and therefore may be used to treat drinking water while in the bottles described above. The primary effects of treatment, and the main anti-microbial mechanisms, are believed to relate to the rich content of broad spectrum ultraviolet light, and the very high-intensity, short-duration nature of the pulses.

Figure 4:
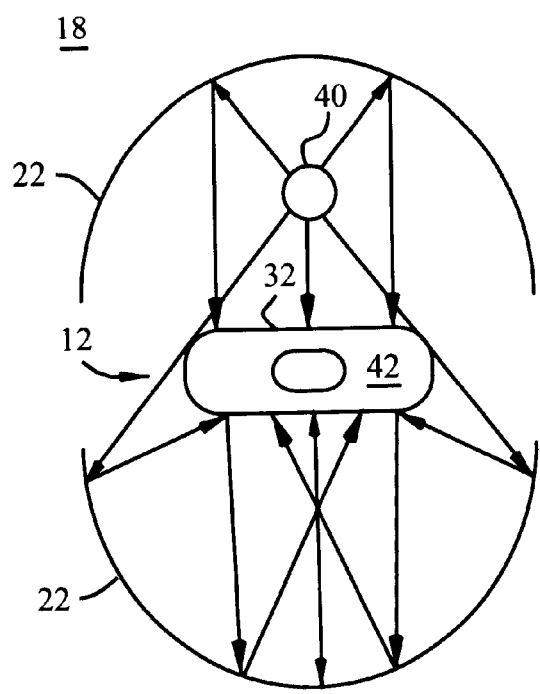
FIG. 4 is an end view of another embodiment of a sterilizing chamber of the of the present invention featuring two reflectors having a drinking water container positioned therein.

Referring next to FIG. 4, an end view is shown of another variation of a sterilizing chamber 18 (or tunnel) of the apparatus FIG. 1. In the variation shown, a pair of reflectors 22 are positioned around a flashlamp 40 and the drinking water container 12, so as to form a tunnel, as a drinking water container 12 is passed through the sterilizing chamber 18 on, for example, a conveyor belt (not shown). The variation shown functions in a manner similar to that in which the variation of FIG. 3 functions except that light passing through, or passing by the drinking water container 12 after being emitted from the flashlamp 40, or reflected from an upper reflector 22, is reflected back toward the drinking water container 12 by a lower reflector 22. Advantageously, this variation maximizes the amount of light impinging upon the drinking water container 12, thereby maximizing the amount of light passing through the drinking water container 12 and drinking water to deactivate microorganisms contained therein.

The methods and apparatuses of the present invention are well suited to sterilization applications wherein, the drinking water is sealed within a polyolefin container 12 prior to illumination of the container 12 with high-intensity, short-duration pulses of incoherent polychromatic light. This advantageously prevents contamination of the interior of the container or the drinking water following treatment (i.e., illumination). Also advantageously, the high-intensity, short-duration pulses of incoherent polychromatic light do not degrade the polyolefin walls of the container 12.

Thus, a terminal sterilization approach is provided for use with a sealed drinking water container that, unlike conventional autoclaving and gamma radiation treatment approaches, does degrade the container being treated.

A common feature, of the possible shapes, designs, arrays, and configurations of products, packaging materials, devices, and treatment chambers should preferably be that the apparatuses, methods, materials, and geometries are arranged so as to provide for or permit the reflection of light not initially absorbed within the product, container, etc. in a manner such that such light can be recycled within the cavity to increase the likelihood of the light finally interacting with or being absorbed by the product or container; or microorganisms, chemicals, or contaminants on or in the product or packaging material.

The degree of success or efficiency of the recycling of the initially unabsorbed light will vary with the apparatuses, materials, methods, and geometries employed.

For example, the cavity quotient or Q (the ratio of energy loss per cycle versus the energy stored in the cavity) will vary based upon the pulsed light wavelengths employed, the reflectivity of the cavity walls, the ability of the cavity to refocus the light back to useful product surfaces or volume, etc.

However, preferably in all instances the cavity will provide an increase in fluence-per-flash and an enhancement in efficiency by providing for some re-utilization of initially unabsorbed light.

For a container and/or product and treatment chamber design that are such that pulsed light within the particular frequency spectrum used for sterilization can reach all the important volumes and surfaces, pulsed light sterilization is dependent upon the spectral content of each flash, the energy of each flash (or fluence-per-flash in Joules/cm$^2$/flash), and the number of flashes delivered. Advantageously, these three parameters are relatively easily and reliably measurable during pulsed light treatment. These three parameters, in accordance with the present embodiments are monitored, controlled, and verified during pulsed light treatment operations. This monitoring, controlling, and verifying proper treatment can then be used for validation of the treatment, i.e., verification that sufficient deactivation is achieved.

Specifically, such monitoring, controlling and verifying of proper treatment allows validation of treatment based on measurements of these three parameters alone, as opposed to observation of the containers or products treated for microbial activity following a waiting period.

These principles are advantageously captured and applied in, for example, the embodiment shown in FIG. 4. The pair of reflectors 22 are positioned around one or more flashlamps 40 and the drinking water container 12, so as to form a tunnel, as the drinking water container 12 is passed through the sterilizing chamber 18 on, for example, a conveyor belt (not shown). This maximizes light reflection inside the tunnel and maximizes exposure of the container 12.

As discussed in the previously incorporated patent applications Ser. Nos. 08/846,102 and 09/326,168, the materials, methods, and geometry of the treatment arrangement can be configured to optimize and elevate the efficiency of the pulsed light process and its attendant killing effects to achieve sterilization during pulsed light disinfection. The effectiveness of such pulsed light sterilization is dependent upon the spectral content of each flash, the energy of each flash (or fluence-per-flash in Joules/cm$^2$/flash).

With further reference to, for example, FIG. 4 a reflective cavity constructed of a broadband reflective material and designed to contain a pulsed light source can be used to increase the effective fluence-per-flash, and accordingly the microbial deactivation effects of pulsed light treatment. As a result of such arrangement, pulsed light not directly incident on the container 12 is reflected and essentially "recycled" within the reflective cavity to eventually interact with the product. Similarly pulsed light passing through the container and product is reflected and "recycled" within the reflective cavity to again interact with the product. This "recycling" of the pulsed light results in a higher effective fluence-per-flash than would be observed absent the reflective cavity.

Such a reflective cavity, i.e., a reflective cavity exhibiting this "recycling" capability may have many shapes and designs. For example, the reflective cavity could be elliptical in shape with the pulsed light source located at one focus of the ellipse, and the product to be treated located at the other focus. Additionally, the reflective cavity can be paraboloidal in shape. Alternately the reflective cavity could be shaped or patterned to facilitate the return of non-absorbed light back onto or into the drinking water container being treated, or to reflect varying fluence levels at various parts of the drinking water or container being treated.

Similarly, the structure containing the drinking water to be treated may be of many types, shapes, materials, and designs. For example, the drinking water may be conveyed through the reflective pulsed light treatment chamber by flowing the water through the chamber in a light transmissive tube. Thus, variations on the embodiments described herein may have as their design goal the treatment of the surface of a container, the surface of a container and the drinking water within, or the volume of the water itself. A wide array of cavities are thus contemplated by the inventors named herein.

In order to provide effective sterilization of drinking water and drinking water containers with pulsed light, it is important not only that the pulsed light reach all the important surfaces of the container and/or volumes of drinking water, but also that such pulsed light be of sufficient strength and duration to accomplish the desired level of deactivation and/or sterilization. Optimization of the pulsed light requires consideration of the spectral content of each flash of light, the energy of each flash (or fluence-per-flash in Joules/cm$^2$/flash) and the number of flashes delivered. Advantageously, embodiments of the present invention provide apparatus and methods wherein these three parameters are reliably measured during pulsed light treatment and the measurements thereof are used to control the sterilization process. In accordance with preferred embodiments herein, these three parameters and/or other relevant parameters are monitored, controlled, and verified during pulsed light treatment operations, thereby allowing for validation of the treatment, i.e., verification that sufficient sterilization is achieved. This validation of the sterilization treatment can, advantageously, be based on measurements of the described parameters alone, as opposed to being based upon observation of the treated products or containers for signs of microbial activity following a waiting period.

Figure 5:
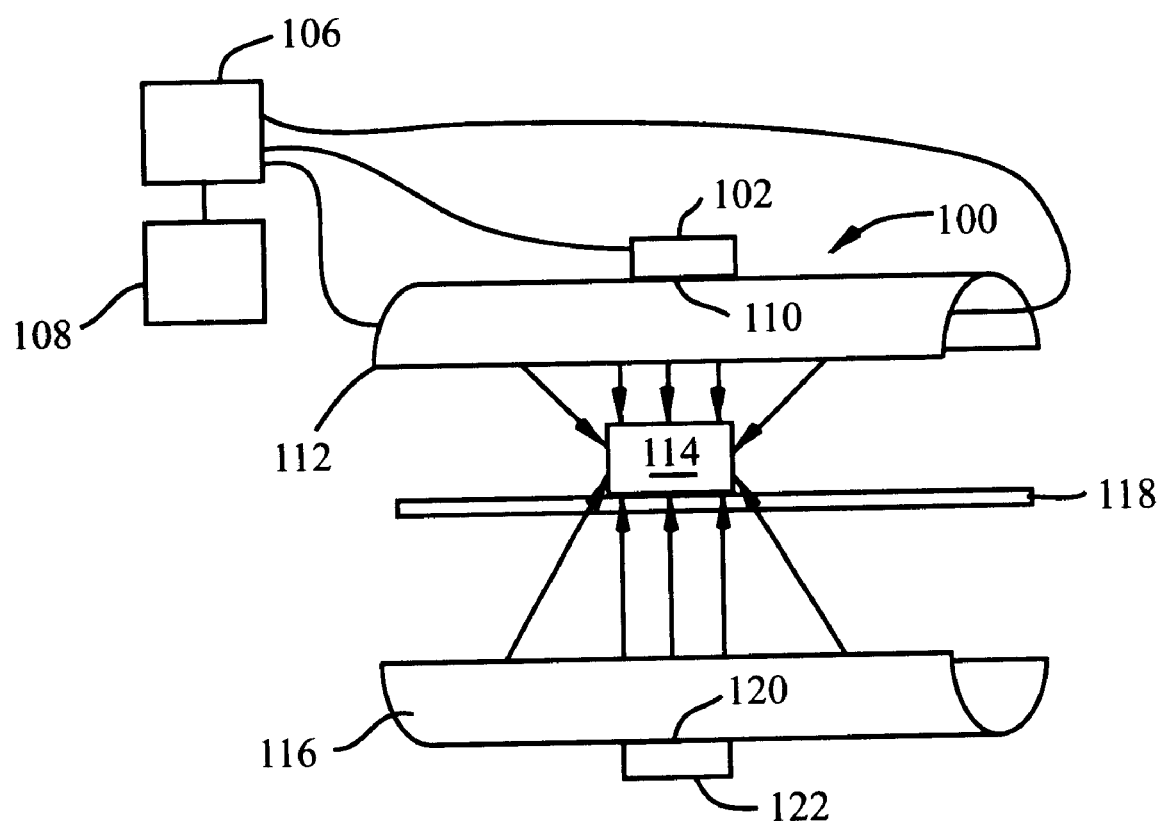
FIG. 5 is a perspective view of a sterilizing chamber, such as the sterilizing chamber of FIG. 4, wherein a photodetector is used to measure the character of the treatment light, such as fluence per flash, in order to maintain parametric control over sterilization of drinking water containers and their contents in such sterilization chamber.

Referring first then to FIG. 5, illustrated is an apparatus for sterilizing a drinking water container in accordance herewith, wherein the sterilization is parametrically controlled. The drinking water container 114 is located within the sterilization chamber, sitting on top of shelf 118 which is formed of material selected to be at least about 10% transmissive, preferably at least about 50% and more preferably at least about 90% transmissive to light in a spectrum containing wavelengths selected from between about 120 nm to about 2600 nm, e.g., wavelengths between about 180 nm to about 1500 nm, e.g., between about 180 nm and about 300 nm. Examples of suitable material for the shelf include, without limitation, quartz and sapphire.

Surrounding the target drinking water container 114 and shelf 118 are flashlamps (not illustrated), which flashlamps are preferably surrounded by reflector systems 112, 116. The reflector system is used to focus or concentrate the light onto the drinking water container 114 to be treated. In the illustrated embodiment, a photodetector 102 is positioned on the reflector system over a pinhole 110, through which pinhole light from a flashlamp passes. Monitor and control circuitry 106 receives data from the photodetector 102 and monitors preselected operating parameters from the flashlamp. Based upon this information, the monitor and control circuitry 106 controls the operation of the flashlamp. Suitable monitor and control circuitry are well known in the art, including for example those systems set forth and incorporated by reference in U.S. Ser. Nos. 09/326,168 and 08/846,102. Data acquisition and control cards added to a personal computer 108 may be used.

In the preferred embodiment illustrated in FIG. 5, there are pinholes 110, 120 and photodetectors 102, 122 employed on the reflector system over each flashlamp. Thereby monitoring and controlling the operation of each individual flashlamp to optimize sterilization of the entire surface and/or volume of the drinking water container 114. It will be appreciated by those of skill in the art that the photodetectors or other detection apparatus may alternatively be placed elsewhere within the sterilization chamber 100, but is preferably placed such that no portion of the detection apparatus interferes with or blocks any portion of the path of the treatment light towards the object. It will be further appreciated, by those of skill in the art, that the entirety of the sterilization chamber is not illustrated in FIG. 5, for example, the exterior shell, doors and/or other means for inserting and removing the target object from the sterilization chamber are not shown. However, such apparatus is well known, examples of which are readily available, for example, from PurePulse Technologies, Inc. of San Diego, Calif. as PUREBRIGHT Model No. PBS-1 as well as previously described, for example, in U.S. Pat. No. 5,900,211, issued on May 4, 1999 to Dunn, et al., which patent is hereby incorporated by reference in its entirety.

Instantaneous, on-line monitoring and evaluation of each flash of the pulsed light treatment process can be performed at the drinking water, the drinking water container, the device or other any other chosen target object. For transmissive drinking water containers, the light going through the drinking water and container can be measured both for fluence-per-flash (or flash peak power) and for spectral content. For drinking water and drinking water containers that are not transmissive in the wavelengths of interest, reflection off of the drinking water or drinking water container can be similarly measured. In both instances the measurement can be performed at one or a multiplicity of sites, or alternatively in a volumetric mode where a large area or volume of the container or container illumination area or volume is sampled through the use of lenses or other mechanisms capable of collecting light over a large angle. In this way pulsed light treatment can be favorably monitored, controlled (through appropriate closed loop feedback control systems), and verified. Thus, not only can each treatment flash be sampled and confirmed as having a minimally sufficient fluence-per-flash and minimally sufficient spectral content, but the fluence-per-flash and spectral content of the light received by the product or container is also monitored in accordance with the present embodiments. This monitoring is performed in an instantaneous, on-line fashion permitting the highest levels of parametric control and verification of drinking water sterility.

With continued reference to FIG. 5, a treatment chamber 100, wherein a photodetector is used to measure fluence-per-flash of light emitted from a flashlamp 104, in order to maintain parametric control over sterilization of drinking water containers and drinking water contained therein in the treatment chamber 100 is shown. The photodetector 102 along with suitable monitor and control circuitry 106 monitors and controls fluence-per-flash, i.e., energy-per-flash, within a prescribed spectral bandwidth, total energy over some preselected treatment time, spectral energy within a preselected bandwidth over time, and/or any of a range of other detectable parameters. In a similar fashion the pulse parameters involved in energizing the flashlamp 104, such as current, peak current, current waveshape, voltage, voltage waveshape, and/or any of a range of other pulse parameters may be monitored and controlled by the monitor and control circuitry 106, such as is known in the art. The output from the monitor and control circuitry 106 monitoring both the flashlamp energizing components and parameters, and the resulting flash parameters completely describe the operation of pulsed light generation within the treatment chamber 100. Suitable monitor and control circuitry 106 is readily available, such as data acquisition and control cards that can be added to a personal computer 108. Electronic output of the monitor and control circuitry 106, in combination with appropriate programmatic control by the personal computer 108, can be used to monitor, adjust, and document pulsed light treatment. By providing instantaneous electronic signals indicative of parameters related to system operation, in the presence of operation or output outside of a preselected range, feedback circuits in the monitor and control circuitry 106 and programmatically embodied in the personal computer 108 can easily be arranged to adjust system operating parameters and output in accordance with well known feedback/control system approaches.

For example, ultraviolet output from the flashlamp 104 can be coupled to lamp voltage and current operating circuitry in the monitor and control circuit 106 through appropriate feedback/control system circuitry. By monitoring ultraviolet output, system performance can be monitored, adjusted, and maintained each in preselected minima and maxima by coupling this information to circuit pulses through appropriate feedback control system circuitry. Similarly, fault detection circuitry within the monitor and control circuitry 106 can be used to summon an operator, shut down the system, or otherwise perform system oversight and alert operations should pulse or output parameters fall below or outside desired levels. In addition, quality control documentation can be performed on-line and in an instantaneous fashion by feeding the electronic signals from operation monitoring systems and output monitoring systems into the personal computer 108 or other computer or electronic storage device.

For pulsed light treatment, a wide range of photodetectors and photooptics may be adapted in a variety of ways to monitor, control, and verify that proper pulsed light sterilization treatment has been achieved. For example, a variety of photooptical methods and detectors are available that can be used to "look at" or interrogate each treatment flash to confirm that the light pulse produced was of the desired intensity, and contained the proper spectral distribution and content. Components for appropriate monitor and control systems are available from a variety of sources and one skilled in the art of photodetector or photooptical systems can design and assemble appropriate systems. For example, surface or volume absorbing calorimeter systems that can be used to monitor the pulsed light fluence per flash or total light output are available from many sources (Gentec, Ophir, Molectron, Digirad, etc.). Similarly, photodetector systems that alone or in combination with appropriate filters or other components are widely available (Hamamatsu, Phillips, EG&G, UDT Sensors, etc.) and can be used to examine the UV content or spectral distribution of the pulsed light flash. The pulsed light can be collected and monitored using a wide variety of means. For example, fiber optic probes, focusing or defocusing lenses, integrating spheres, CCD arrays, etc. can be used to collect light from wide or narrow angles or provide spatial resolution of multipoint analysis for the light imaging system. Components or systems for light collecting, handling, monitoring and analyzing are available from many sources; and these components or systems can be designed and assembled by and from a large number of manufacturers or suppliers.

A simple method of quantifying the light signature of a pulsed light treatment flash is shown. A sample of the light flash is collected via a small diameter hole 110, or "pinhole" 110, located in a reflector 112 system used to focus or concentrate the light onto the target object to be treated. The pinhole 110 in the reflector 112 transmits light to one or more light sensitive devices (photodetectors 102), such as photometer, a photomultiplier, a calorimeter, a pyroelectric joulemeter, a bolometer, a diode or diode array, or other photosensitive or photodetector system. The photodetector 102 can be used to sample the character (e.g., fluence-per-flash and spectral content) of the treatment light through a variety of means. The light can be "viewed" directly or passed through a sampling port, lens, or likewise apertured, collimated, filtered, focused, defocused, reflected, refracted, or otherwise handled, manipulated, or collected before evaluation.

One, or more photodetectors can interrogate the treatment light from the flash lamp with or without an appropriate filter or filters so that fluence-per-flash and/or spectral distribution can be monitored and controlled.

The signal from the photodetector 102 varies temporally with the fluence-per-flash, and with an appropriate filter or filters such can be specific to a particular portion of the light spectrum. For example, since the ultraviolet fluence-per-flash is generally of importance, the photodetector 102 can measure the fluence-per-flash of only the ultraviolet portion of the spectrum through the use of an appropriate ultraviolet bandpass filter. The output of the photodetector 102 can be integrated so as to measure the total ultraviolet energy of the light pulse in the selected bandwidth. This integrated signal is then recorded by either a computer or other means to provide a permanent record of the total energy of the light pulse, and, over time, the entire pulsed light treatment process.

Embodiments of the present invention may be calibrated. For example, an ultraviolet calorimeter is placed in the treatment chamber in place of drinking water container. The calorimeter measures the ultraviolet energy of the light pulse, and is traceable back to international standards. Measurements taken by the calorimeter can thus be compared to measurements taken by the photodetector, so as to calibrate the photodetector to international standards. In a second approach, the light passing through or reflected from the container is measured by the calorimeter.

In general for treatment with pulses of light, containers must be moved through the treatment area in such a manner that the complete container is treated. For transparent containers, the process becomes more complex due to internal reflection and refraction of the light as it passes into the container. The following are some particular examples of container transport approaches.

Figure 6:
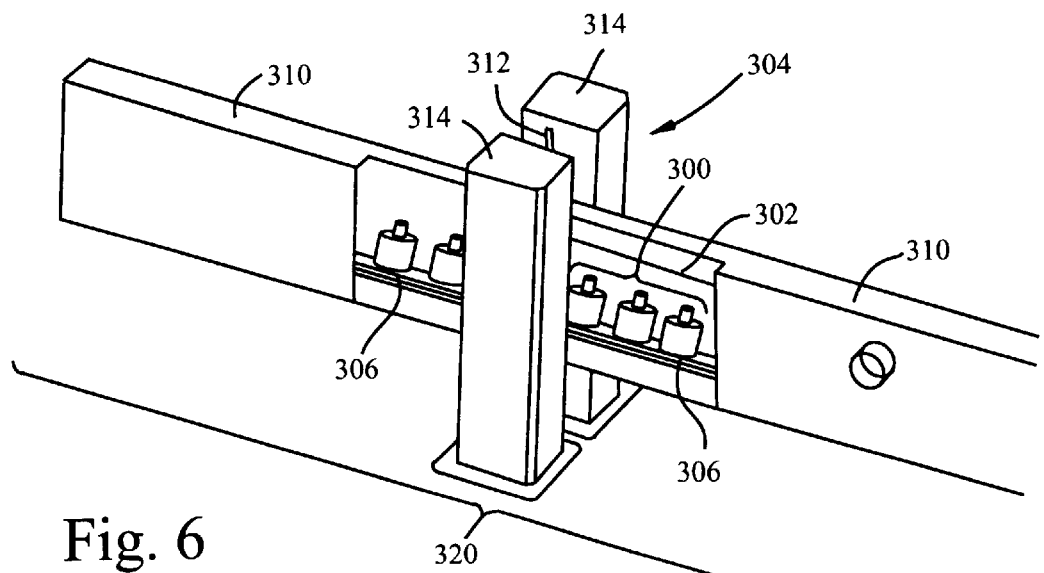
FIG. 6 is a perspective view of several blow-fill-seal containers, an additional variation of the sterilization chamber (or tunnel) of the apparatus of FIG. 1, and a transport approach for moving the containers through the sterilization chamber.

FIG. 6 is a perspective view of a sterilizing apparatus 320 including a transport approach (e.g., a conveyor belt) 306 for moving the containers (e.g., drinking water bottles) 300 through a treatment chamber 304. Also present, but not shown, are photodetectors or other detectors that provide monitoring control, and verification of the treatment process. Monitoring and control circuit (not shown) and a computer (not shown) are also used for monitoring control and verification. The term bottles should be applied broadly herein, including without limitation, bags, cartons, glass bottles, and plastic bottles.

In operation, the drinking water bottles 300 can enter the treatment chamber 304 through a tunnel 310. The tunnel 310 is designed to contain pulses of light produced by flashlamps 312 so as to protect operators. A photoeye (not shown) is used to detect the presence of a drinking water bottles 300 in response to which the pulses of light are initiated automatically, preferably after a delay to assure that the drinking water bottles 300 are in proper position for treatment. The flashlamps 312 are located within reflector housings 314 on both sides of the drinking water bottles 300 to assure complete treatment. The flashlamps 312 are fired simultaneously to maximize fluence-per-flash for increased sterilization effectivity as illustrated in the examples above.

Figure 7:
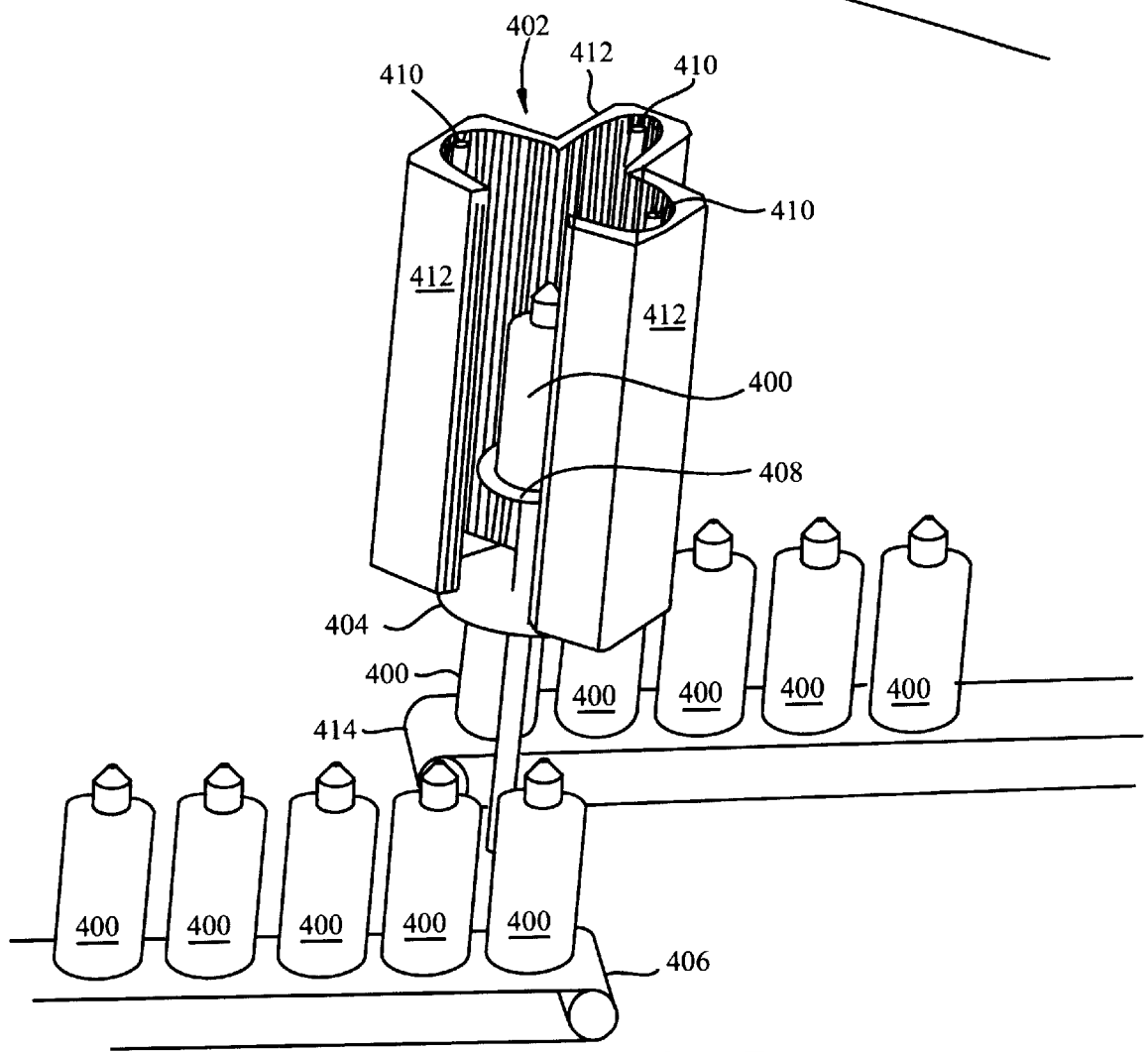
FIG. 7 is a perspective view of several drinking water containers, a further additional variation of the sterilization chamber of the apparatus of FIG. 1, and a transport approach for moving the drinking water containers through the sterilization chamber.

Referring to FIG. 7, a perspective view is shown of several drinking water bottles 400, a further additional variation of the treatment chamber 402, and a transport apparatus 404 for moving the drinking water bottles 400 through the treatment chamber 402. Also present, but not shown, are photodetectors or other detectors that provide monitoring control, and verification of the treatment process. Monitoring and control circuit (not shown) and a computer (not shown) are also used for monitoring control and verification.

The drinking water bottles 400 are carried on a first conveyor 406 to the treatment chamber 402. A transfer device (not shown) moves the drinking water bottles 400 over off a first conveyor 406 onto a platform 408. The platform 408 moves the drinking water bottles 400 up and into the treatment chamber 402. The treatment chamber 402 includes four flashlamps 410 and four corresponding reflectors 412 (one of each of which have been omitted from FIG. 12 to permit viewing of the drinking water bottle 400 on the platform 408) arranged in what is roughly quadracylindrical arrangement, i.e., four elongated bulbous lobes arranged with adjacent edges juxtaposed against one another. All of the flashlamps 40 are preferably flashed simultaneously in order to maximize fluence-per-flash and thus deactivation of microorganisms. Also, the reflectors 412 are designed to form a high Q treatment chamber 402, and thus to make maximum usage of the pulses of light emitted from the flashlamps. Following one or more flashes of the flashlamp 410, the platform 40 is lowered and a new drinking water bottle 400 is moved into place by the transport mechanism (not shown), as the initial drinking water bottle 400 is moved onto a second conveyor 414.

In this way, an effective method is provided for sterilizing, not only drinking water bottles 12, but water contained therein, without requiring the high temperature processes involved in autoclaving. As a result, materials such as olefins, nylon, and composite materials may advantageously be employed in drinking water bottles. Furthermore, the present embodiment achieves a sterility assurance level of at least $10^{-6}$, and does not require the use of gamma radiation or other highly degradative processes.

Figure 8:
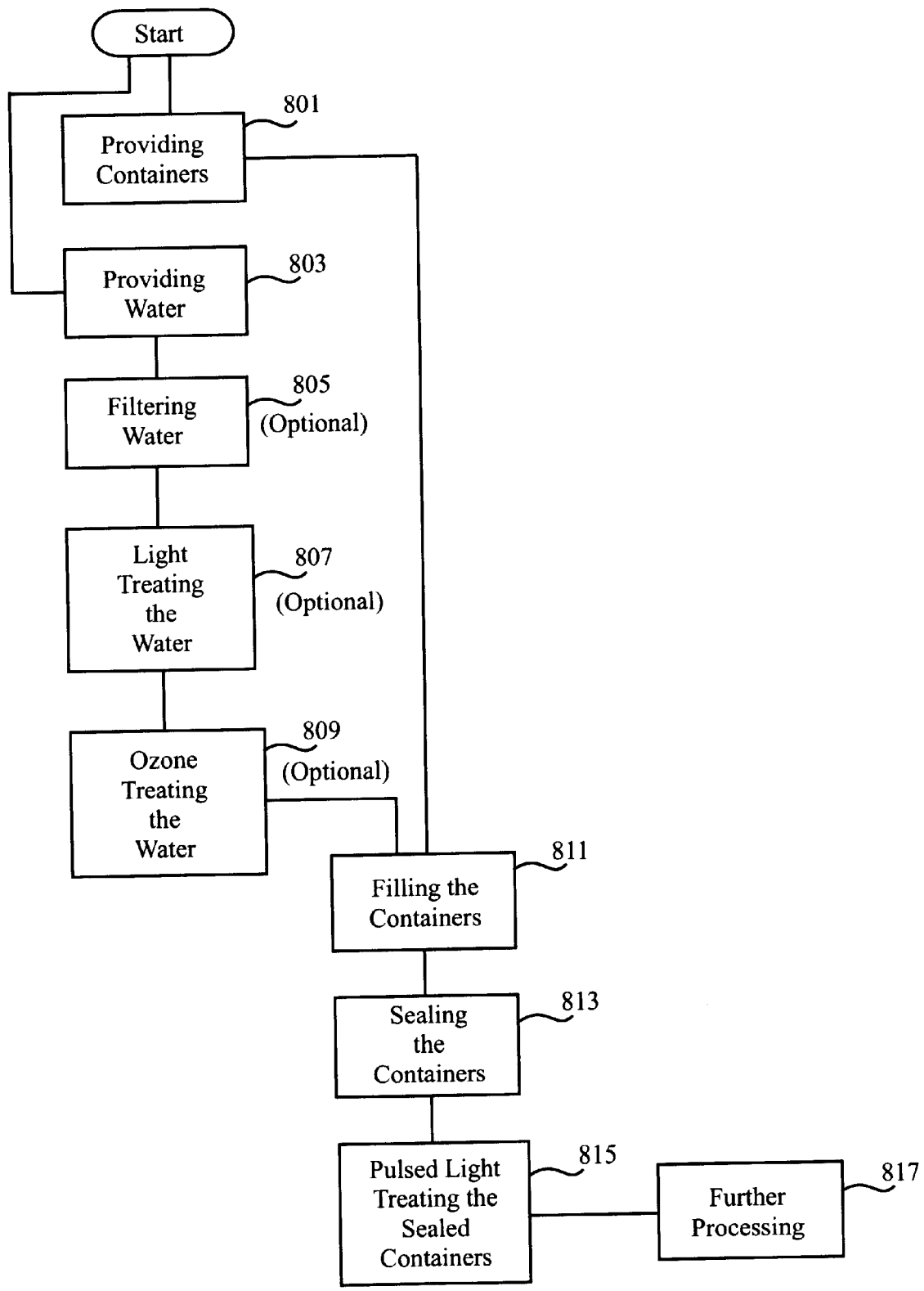
FIG. 8 is a flowchart describing an embodiment for processing drinking water and drinking water containers in accordance with the present invention.

A preferred method of treating drinking water to deactivate microorganisms is described with reference to the flowchart illustrated in FIG. 8. The process begins by providing drinking water containers (of the type discussed herein)(Step 801) and providing water (Step 803). The water may be optionally be treated (Steps 805, 807, 809) by filtration, light treatment (decontamination), and ozone treatment. The containers are then filled with drinking water (Step 811) and sealed (Step 813). The sealed containers are treated with short duration broad band light pulses to deactivate microorganisms (Step 815). These sealed and sterilized containers are the subject to further processing as needed, for example, labeling the containers (Step 817).

The optional filtration may be accomplished by a variety of means known to those having ordinary skill in the art (Step 805). For example, the water can be repeatedly filtered using a series of filters beginning with a multimedia filter, followed by an activated carbon filter, and finally filtered with a micro-porosity filter (e.g., a 1 $\mu$m filter). A light treatment step using UV light or even broad-band pulsed light can be used to treat the drinking water (Step 807). The water can then be treated by ozone injection (Step 809). Once treated in this way, the water is provided to a container filling apparatus which fills the drinking water containers with drinking water, after which they are sealed, then light treated (Steps 811, 813, 815).

While the invention herein disclosed has been described by means of specific embodiments and applications thereof, numerous modifications and variations could be made thereto by those skilled in the art without departing from the scope of the invention set forth in the claims.

We claim:

1. An apparatus for sterilizing microorganisms in a drinking water container comprising:

said drinking water container, wherein said drinking water container transmits light in a spectrum of from between 180 nm and 380 nm; and a flashlamp system including means for generating high-intensity, short-duration pulses of polychromatic light in a broad spectrum, and for deactivating microorganisms within said container by illuminating said container with the pulses of light having been generated.

2. The apparatus of claim 1 wherein said drinking water container consists of a polyolefin.

3. The apparatus of claim 1 wherein said drinking water container includes polyethylene.

4. The apparatus of claim 1 wherein said drinking water container is at least one percent transmissive to light having a wavelength of about 260 nanometers.

5. The apparatus of claim 1 wherein said means for deactivating includes means for achieving a sterility assurance level of at least $10^{-6}$.

6. The apparatus of claim 1 wherein:

said drinking water container includes an input port; and wherein said flashlamp includes means for deactivating microorganisms within the input port by illuminating the input port with the pulses of light having been generated, and for deactivating microorganisms at the input port by illuminating the input port with the pulses of light having been generated.

7. An apparatus as in claim 6 wherein said input port includes a threaded means for securing a cap to said drinking water container.

8. The apparatus of claim 7, wherein the drinking water container transmits more than about one percent of light at a wavelength of 260 nm.

9. An apparatus for deactivating microorganisms in a drinking water container comprising:

the drinking water container, wherein the container includes at least one input port through which the drinking water can be introduced into said drinking water container, and wherein the drinking water container and input port transmit light in a spectrum of from between about 120 nm and about 2600 nm; and a flashlamp system including means for generating high-intensity, short-duration pulses of polychromatic light in a broad spectrum, and for deactivating microorganisms within the drinking water container by illuminating the drinking water container with the pulses of light having been generated, said means for deactivating including means for achieving a sterility assurance level of at least $10^{-6}$.

10. The apparatus of claim 9 wherein said drinking water container and said at least one input port include polyethylene.

11. The apparatus of claim 9 wherein said drinking water is at least one percent transmissive to light having a wavelength of 260 nanometers.

12. An apparatus for sterilizing microorganisms within a drinking water container comprising:

the drinking water container enveloping drinking water contained therein, wherein the container transmits light in a spectrum of from between 180 nm and 380 nm;

a flashlamp system for generating high-intensity, short-duration pulses of polychromatic light in a broad spectrum, for directing the pulses of polychromatic light at the container and for deactivating microorganisms within the container by illuminating the container with the pulses of light having been generated;

a photo-sensitive detector, positioned so as to receive a portion of each of the pulses of light as a measure of an amount of light illuminating the product, and for generating an output signal in response thereto; and a control system, coupled to the flashlamp system and the photo-sensitive detector, for determining, in response to the output signal, whether the pulses of light are sufficient to effect a prescribed level of deactivation of microorganisms in the drinking water container.

13. The apparatus of claim 12 wherein drinking water container enveloping drinking water comprises a drinking water bottle.

14. The apparatus of claim 13 wherein the control system further comprises means for monitoring another output signal indicative of a pulse parameter and for further determining whether, in response to the other output signal, the pulse parameter is sufficient to generate pulses of light that effect a prescribed level of deactivation of microorganisms within said drinking water bottle.

15. The apparatus of claim 14 wherein the control system further comprises:

monitor and control circuitry; and a computer including software.

16. The apparatus of claim 14 wherein said control system comprises means for monitoring the other output signal, wherein the other output signal is indicative of a pulse parameter selected from a group of pulse parameters consisting of current, voltage, peak current, current waveshape, peak voltage and voltage waveshape.

17. The apparatus of claim 12 wherein said photosensitive detector generates said output signal, wherein said output signal is indicative of a photo parameter selected from a group of photo parameters consisting of total fluence-per-flash, fluence-per-flash, total energy over time, and energy within a preselected bandwidth over time.

18. The apparatus of claim 17 wherein said control system comprises:

monitor and control circuitry; and a computer including software.

19. The apparatus of claim 12 wherein said control system includes means for determining, in response to the output signal, whether the pulses of light are of at least a prescribed fluence per flash.

20. The apparatus of claim 19 wherein said control system includes means for determining, in response to the output signal, whether the pulses of light are of at least a prescribed fluence per flash within a prescribed frequency band.

21. The apparatus of claim 12 wherein said means for deactivating includes means for achieving a sterility assurance level of at least $10^{-6}$.

22. The apparatus of claim 12 wherein said means for deactivating includes means for achieving a sterility assurance level of at least $10^{-3}$.

23. The apparatus of claim 13 wherein said flashlamp system includes a reflector at least partially surrounding a flashlamp bulb and said drinking water bottle for reflecting the pulses of light toward said bottle and for reflecting at least a portion of light transmitted through said bottle back toward said bottle.

24. The apparatus of claim 14 further comprising:

a reflector positioned proximate to the flashlamp for reflecting the pulses of light toward the said bottle.

25. The apparatus of claim 24 further comprising:

a hole located in said reflector and in which the photo-sensitive device is positioned.

26. The apparatus of claim 12 wherein said container contains drinking water transmissive of more than about one percent of light at a wavelength of 260 nm.

27. The method of claim 26 wherein said determining whether the pulses of light are sufficient includes determining whether the pulses of light are of at least a prescribed fluence per flash.

28. The method of claim 26 wherein said determining whether the pulses of light are sufficient includes determining whether the pulses contain at least a prescribed spectral content.

29. The method of claim 26 wherein said deactivating includes achieving a sterility assurance level of at least $10^{-6}$.

30. The method of claim 26 wherein said deactivating includes achieving a sterility assurance level of at least $10^{-3}$.

31. The method of claim 26 further comprising:
reflecting at least a portion of each pulse of light toward the bottle.

32. An apparatus for sterilizing microorganisms at a surface of a drinking water bottle, the apparatus comprising:
a flashlamp system for generating high-intensity, short-duration pulses of polychromatic light in a broad spectrum, and for deactivating microorganisms on the surface of the said drinking water bottle by illuminating the surface of the drinking water bottle with the pulses of light having been generated;
a photo-sensitive detector, positioned so as to receive a portion of each of the pulses of light as a measure of an amount of light illuminating the surface of the drinking water bottle, for generating an output signal in response thereto; and
a control system, coupled to the flashlamp system and the photo-sensitive detector, for determining, in response to the output signal, whether the pulses of light are sufficient to effect a prescribed level of deactivation of microorganisms on the surface of the drinking water bottle.

33. The apparatus of claim 32 wherein the control system further comprises means for monitoring another output signal indicative of a pulse parameter and for further determining whether, in response to the other output signal, the pulse parameter is sufficient to generate pulses of light that effect a prescribed level of deactivation of microorganisms on the surface of the drinking water bottle.

34. The apparatus of claim 33 wherein the control system further comprises:
monitor and control circuitry; and
a computer including software.

35. The apparatus of claim 33 wherein said control system comprises means for monitoring the other output signal, wherein the other output signal is indicative of a pulse parameter selected from a group of pulse parameters consisting of current, voltage, peak current, current waveshape, peak voltage and voltage waveshape.

36. The apparatus of claim 32 wherein said photosensitive detector generates said output signal, wherein said output signal is indicative of a photo parameter selected from a group of photo parameters consisting of total fluence-perflash, fluence-per-flash, total energy over time, and energy within a preselected bandwidth over time.

37. A method for sterilizing microorganisms within a drinking water container comprising:
generating a high-intensity, short-duration pulse of polychromatic light in a broad spectrum;
deactivating microorganisms within the container by directing the pulse of light having been generated at the container enveloping the drinking water, the container transmitting light in a spectrum of from between 180 nm and 380 nm;
receiving a portion of the pulse of light as a measure of an amount of the pulse of light illuminating the container;
generating an output signal in response to the receiving of the portion of the pulse of light; and
determining, in response to the generating of the output signal, whether the pulse of light is sufficient to effect a prescribed level of deactivation of microorganisms in the container.

38. A method for sterilizing microorganisms at a surface of a drinking water container comprising:
generating a high-intensity, short-duration pulse of polychromatic light in a broad spectrum;
deactivating microorganisms at the surface of the drinking water container by directing the pulse of light having been generated at the surface of the drinking water container;
receiving a portion of the pulse of light as a measure of an amount of the pulse of light illuminating the surface of the drinking water container;
generating an output signal in response to the receiving of the portion of the pulse of light; and
determining, in response to the generating of the output signal, whether the pulse of light is sufficient to effect a prescribed level of deactivation of microorganisms in the drinking water container.

39. The method of claim 38 wherein said determining whether the pulses of light are sufficient includes determining whether the pulses contain at least a prescribed spectral content.

40. The method of claim 38 further comprising:
reflecting at least a portion of each pulse of light toward the surface of the drinking water container.

41. A method for treating drinking water comprising:
providing a sealed drinking water container containing drinking water, wherein the sealed drinking water container transmits light in a spectrum of from between 180 nm and 380 nm; and
treating said sealed container with a high-intensity, short-duration pulse of polychromatic light in a broad spectrum to deactivate microorganisms contained within the sealed container.

42. A method as in claim 41 wherein said step of providing a sealed drinking water container containing drinking water further comprises the steps of:
providing open unfilled drinking water containers;
providing drinking water;
filtering said drinking water;
exposing said drinking water to light treatment;
ozone treating said drinking water;
filling said drinking water containers with said drinking water; and
sealing said drinking water inside said drinking water containers.

43. A method as in claim 42 wherein said step of exposing said drinking water to light treatment includes exposing said drinking water to ultraviolet light.

44. A method as in claim 42 wherein said step of exposing said drinking water to light treatment includes exposing said drinking water to high-intensity, short-duration pulses of polychromatic light in a broad spectrum.

45. The method of claim 41 wherein said step of treating said sealed container with a high-intensity, short-duration pulse of polychromatic light in a broad spectrum to deactivate microorganisms contained within the sealed container includes achieving a sterility assurance level of at least $10^{-6}$.

46. The method of claim 41 wherein said step of treating said sealed container with a high-intensity, short-duration pulse of polychromatic light in a broad spectrum to deactivate microorganisms contained within the sealed container includes means for achieving a sterility assurance level of at least $10^{-3}$.

* * * * *

UNITED STATES PATENT AND TRADEMARK OFFICE
CERTIFICATE OF CORRECTION

PATENT NO. : 6,433,344 B1
DATED : August 13, 2002
INVENTOR(S) : Salisbury et al.

It is certified that error appears in the above-identified patent and that said Letters Patent is hereby corrected as shown below:

<u>Column 18,</u>
Line 66, change "method" to -- apparatus --

<u>Column 19,</u>
Lines 3, 7, 9 and 11, change "method" to -- apparatus --

Signed and Sealed this

Twenty-fourth Day of February, 2004

JON W. DUDAS
*Acting Director of the United States Patent and Trademark Office*